(12) United States Patent
Prelewitz

(10) Patent No.: US 7,006,219 B2
(45) Date of Patent: Feb. 28, 2006

(54) BIOLOGICAL IMAGER

(75) Inventor: David F. Prelewitz, Rochester, NY (US)

(73) Assignee: Technology Innovations, LLC, West Henrietta, NY (US)

( * ) Notice: Subject to any disclaimer, the term of this patent is extended or adjusted under 35 U.S.C. 154(b) by 249 days.

(21) Appl. No.: 10/441,837

(22) Filed: May 20, 2003

(65) Prior Publication Data

US 2004/0233452 A1    Nov. 25, 2004

(51) Int. Cl.
    *G01N 21/00* (2006.01)

(52) U.S. Cl. .................... 356/337; 356/338
(58) Field of Classification Search ........ 356/335–343, 356/72, 73, 317, 318, 336; 250/201.9, 208.1
    See application file for complete search history.

(56) References Cited

U.S. PATENT DOCUMENTS

| | | | |
|---|---|---|---|
| 5,331,156 A | | 7/1994 | Hines et al. |
| 5,553,616 A | * | 9/1996 | Ham et al. .................. 600/316 |
| 5,999,250 A | * | 12/1999 | Hairston et al. ............. 356/73 |
| 6,100,976 A | * | 8/2000 | Ackerson .................... 356/336 |
| 6,130,419 A | * | 10/2000 | Neal ....................... 250/201.9 |
| 2002/0101593 A1 | * | 8/2002 | Yang et al. ................. 356/484 |

OTHER PUBLICATIONS

Goodman, Joseph W., Frequency Analysis of Optical Imaging Systems, Introduction to Fourier Optics, 1968, pp. 120-125, McGraw-Hill Book Company.
Fermeglia, Maurizio and Torriano Giovanni, Density, Viscosity, and Refractive Index for Binary Systems of n-C16 and Four Nonlinear Alkanes at 298.15K, Journal of Chemical Engineering Data, 1999, pp. 965-969, vol. 44, No. 5.

* cited by examiner

*Primary Examiner*—Michael P. Stafira
(74) *Attorney, Agent, or Firm*—Stephen B. Salai, Esq.; Thomas B. Ryan; Harter, Secrest & Emery LLP

(57) ABSTRACT

Apparatus and method for quantifying the biological components of a biological system having at least two different refractive indices through detection of wave front distortions. The biological component fractions are determined based on information gathered on their respective indices when exposed to particular wavelengths of light.

14 Claims, 12 Drawing Sheets

OPTICAL LAYOUT

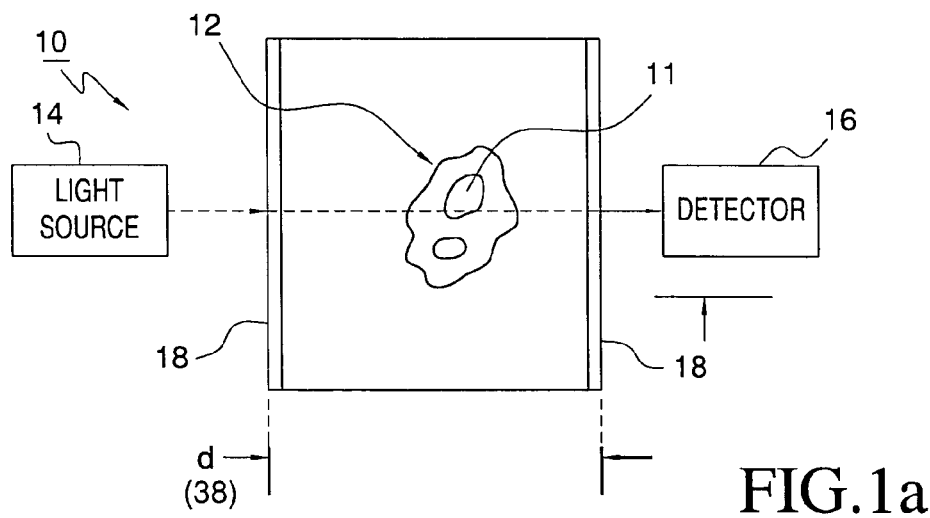
FIG.1a
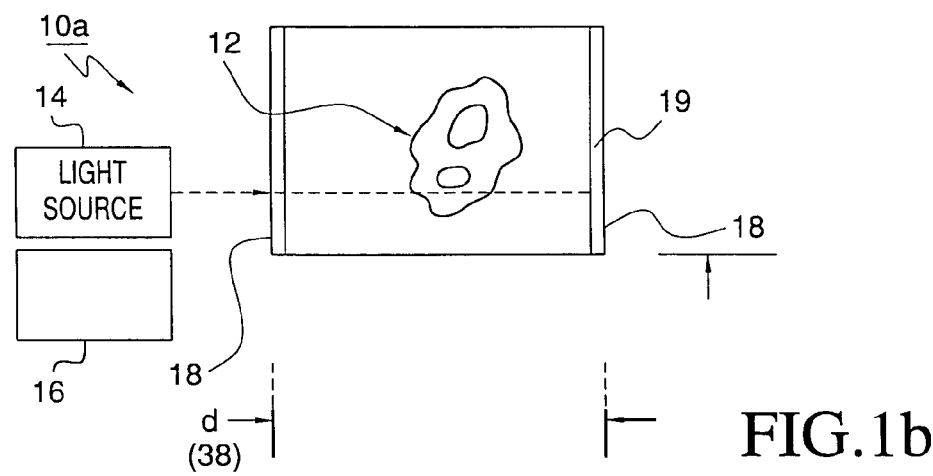
FIG.1b
FIG.7
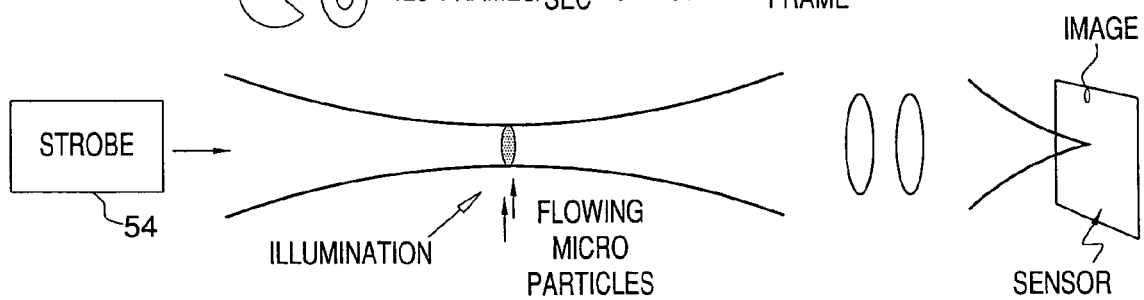

OPTICAL LAYOUT

FIG.2a

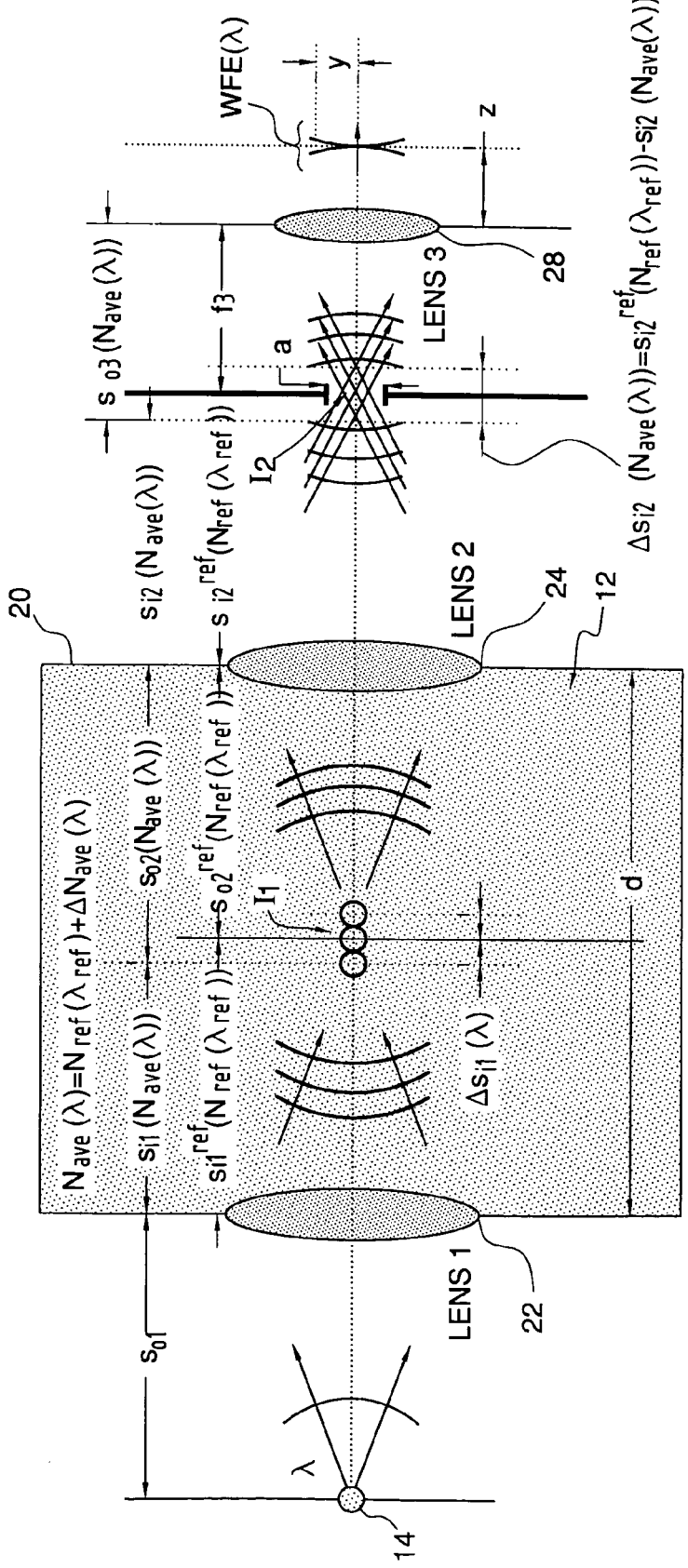

EQUATIONS:

$$WFE(\lambda) = \frac{|s_{i3}(\lambda) - z| - \sqrt{(s_{i3}(\lambda) - z)^2 - y^2}}{\lambda_{ref}} = \frac{1}{\lambda_{ref}}\left[\left|f_3 - \frac{f_3^2}{\Delta s_{i2}(\lambda)} - z\right| - \sqrt{\left(f_3 - \frac{f_3^2}{\Delta s_{i2}(\lambda)} - z\right)^2 - y^2}\right]$$

$$\Delta s_{i2}(\lambda) = s_{i2}^{ref}(\lambda) - s_{i2}(\lambda) = \frac{df_2 - N_{ref}(\lambda_{ref})f_1f_2\, s_{o1}/(s_{o1}-f_1)}{d - N_{ref}(\lambda_{ref})[f_2 - f_1\, s_{o1}/(s_{o1}-f_1)]} - \frac{df_2 - N_{ave}(\lambda)f_1f_2\, s_{o1}/(s_{o1}-f_1)}{d - N_{ave}(\lambda)[f_2 - f_1\, s_{o1}/(s_{o1}-f_1)]}$$

BIOLOGICAL IMAGER

BACKGROUND OF THE INVENTION

1. Filed of the Invention

This invention relates to an apparatus and method for analyzing different components in a system having at least two different refractive indices. This invention further, and more particularly, relates to biological imaging through the components of a biological system.

2. Background Art

In many situations the monitoring of a biological system in real time is desired in addition to determining the biological components without using a computer-intensive technique.

It is desirable to make measurements without having to recalibrate each time a measurement is taken, such as those that use absorption techniques. Different material properties require recalibration of currently used equipment. This invention addresses this problem.

BRIEF SUMMARY OF THE INVENTION

This invention relates to an apparatus and method for analyzing a system using the refractive index of light. The biological component fractions of a biological system are determined using the refractive index of materials in relation to specific wavelengths of light.

The invention can determine the percentages of biological components and water without prior knowledge of the refractive index of the biological components. The method determines the percentages of biological component fractions, include passing a focused light beam through the biological components, measuring the displacement of the point of focus from a known focal point with a known index of refraction, and thereby calculating the percentages of biological components present.

BRIEF DESCRIPTION OF THE SEVERAL VIEWS OF THE DRAWING(S)

FIG. 1a is a diagram of the biological imager of this invention.

FIG. 1b is a diagram of another biological imager.

FIGS. 2 and 2a show schematic diagrams of the biological imager.

FIG. 7 shows a schematic drawing of the strobe and sensor arrangement.

DETAILED DESCRIPTION OF THE INVENTION

Figure 2:
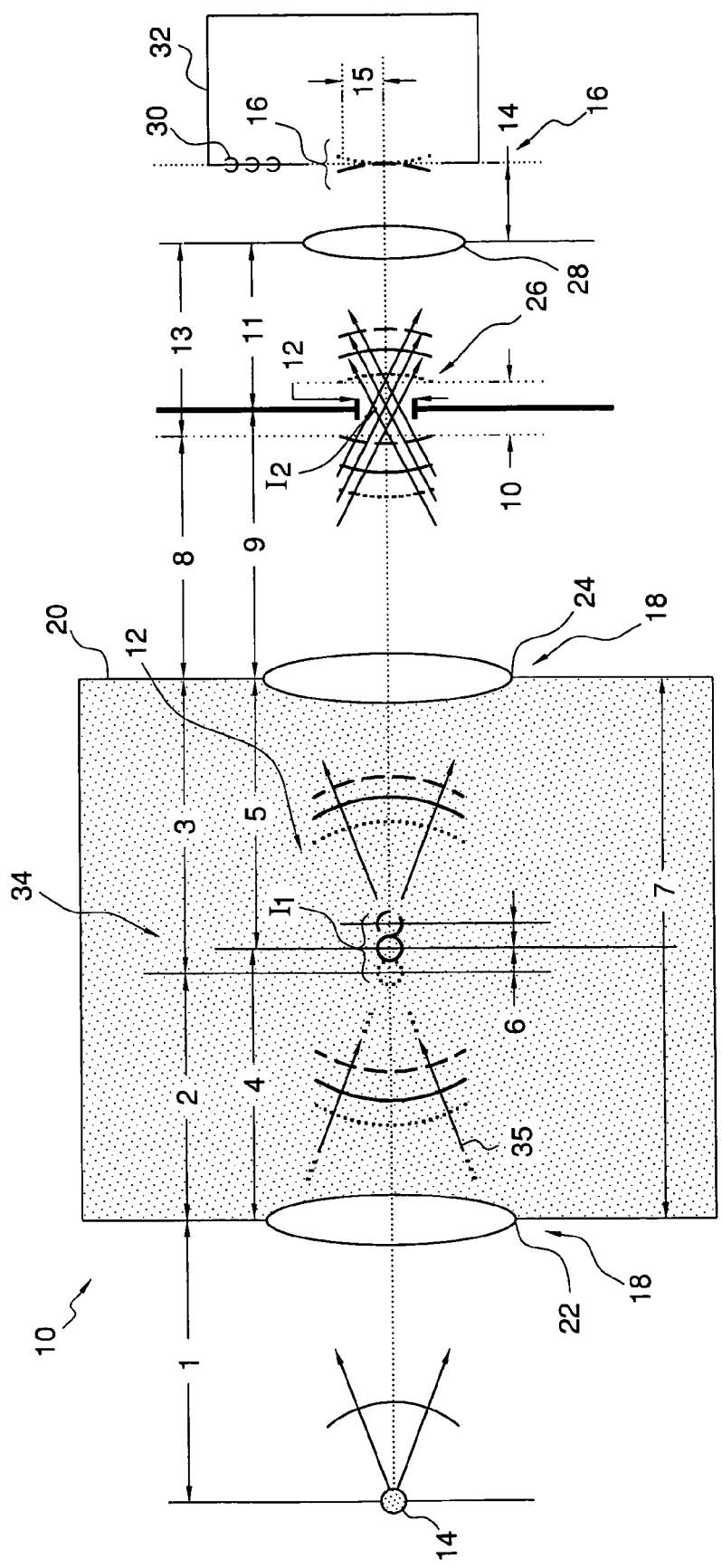

Virtually every biological system consists of a variety of components composed of fluids and gels that exist as a mixture, each component with one or more distinct refractive indices when a specific wavelength of light passes through the mixture. Typically elaborate imaging methods must be used to image these biological systems and to measure their physical properties such as viscosity, geometry, relative fractions, and flow rates if needed.

Fluids and gels, specifically those of different biological components, refract light by varying degrees when a specific wavelength passes through the mixture. The amount of refraction is a function of fluid composition and wavelength of the light passing through the fluid. The refractive index is a physical property of the fluid and is a parameter for determining the optical interaction of the fluid and the light refracted through it.

This invention is applicable to all systems including biological systems. For purposes of brevity, however, the description herein will be primarily directed to invitro biological systems, particularly a cell with components composed of protein matrix-based gels.

FIG. 1a shows a biological imager 10 deployed to analyze a biological mixture of biological components including water, particulate matter, and other materials that could be found in a biological system. FIG. 1 shows a cell 11 with a variety of components such as protein, matrix-based gels hereafter referred to as a biological mixture 12 which could be any system of components but is shown here as a cell. Control of the fluid of the bath, as well as its movement if relevant, is known and can be described in a variety of ways, some of which are not to be discussed in this application.

The biological imager 10 has a light source 14 and a detector 16 arranged on opposite sides of a sample of a biological mixture 12 which is made up of non-immiscible biological components. This mixture must be such that when separated it retains its ratio. The biological imager is such that there are transparent, or partially transparent, openings 18 between the light source and the detector that allow light to pass from the light source through the biological mixture 12 to detector 16. The biological imager 10 can incorporate any number of optical elements, including but certainly not limited to lenses, filters, diffraction gratings, and other optical elements that will be discussed in detail later. These optical elements can be incorporated into the openings 18 or can stand alone.

The light source 14 is a point source or extended point source with one or more discrete wavelengths temporally and/or spatially separated such as would be true for a single source that is pulsed or one or more spatially separated sources. The source can include one or more discrete wavelengths or be a filtered white light source. If there are two or more light sources they can have overlapping spectra but the wavelengths must be at least detectable so that there is sufficient energy that is unique to each wavelength to provide two unique refractive properties after the light has passed through the fluid mixture. Note that alternatively a wideband white light source could be used unfiltered (without discrete wavelengths detectable at the source) and filtered at the detector. What is required is that the two wavelengths must be discrete to provide distinct and separate information when separately focused. Each discrete wavelength will be separately focused and the shift in the focal point measured from a known focal point.

FIG. 1b shows a biological imager 10a to analyze the fluid mixture 12 where the detector 16 is in an alternate location. The biological imager 10a has a second surface 19 that can incorporate the detector 16 or may be reflective or partially reflective such that the detection of a component may be directly read, recorded on the surface 19 or reflected toward another location. This embodiment could incorporate a circuit that diverted the focal point electronically as could the other embodiments.

FIGS. 2 and 2a are detailed schematic diagrams of the biological imager 10 shown in a container 20 which could be a laboratory. The fluid mixture 12 is shown between the light source 14 and the detector 16. In this embodiment there is a first quadradric phase plate ($L_1$) 22 and a second quadradric phase plate ($L_2$) 24 both of which preferably are positive lenses, and hereafter referred to as first lens 22 and second lens 24. Light from the source 14 can be focused in the fluid mixture 12 where a real image ($I_1$) of the source 14 is formed by $L_1$. The light travels on to ($L_2$) which can form another image ($I_2$) near an aperture or spatial filter 26 before being focused by a third collimating lens 28 onto the lens array 30 and an area sensor 32 which could be a focal plane array. It is not necessary that the focus occur in the fluid mixture 12. The volume of the fluid mixture 12 that is being analyzed will be referred as the analysis zone 34 in the following discussion. The analysis zone is also referred to as a capturing cone. The fact that this covers a larger volume allows integration and averaging of a larger volume of fluid mixture 12.

Figure 3A:
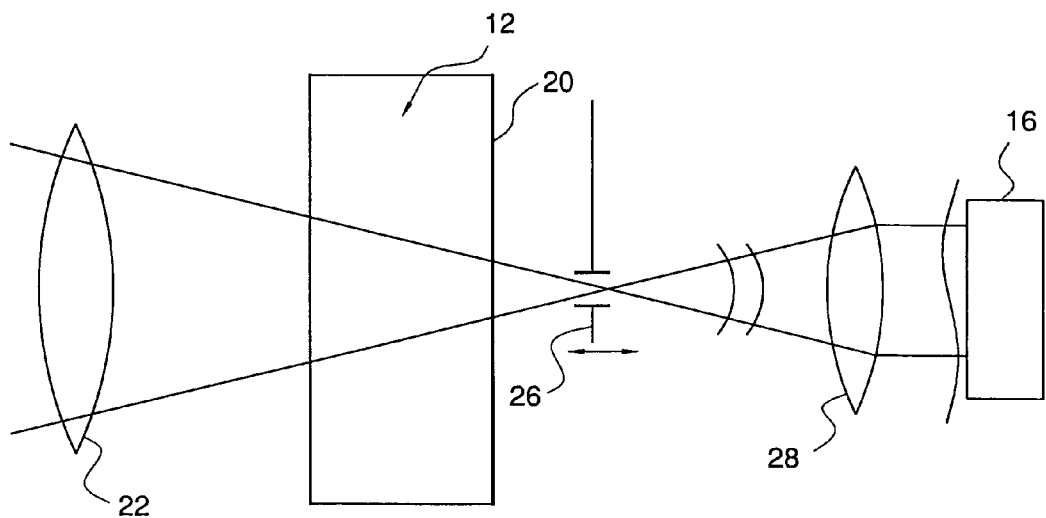
FIGS. 3a–3c show schematic diagrams of the biological imager.
Figure 3B:
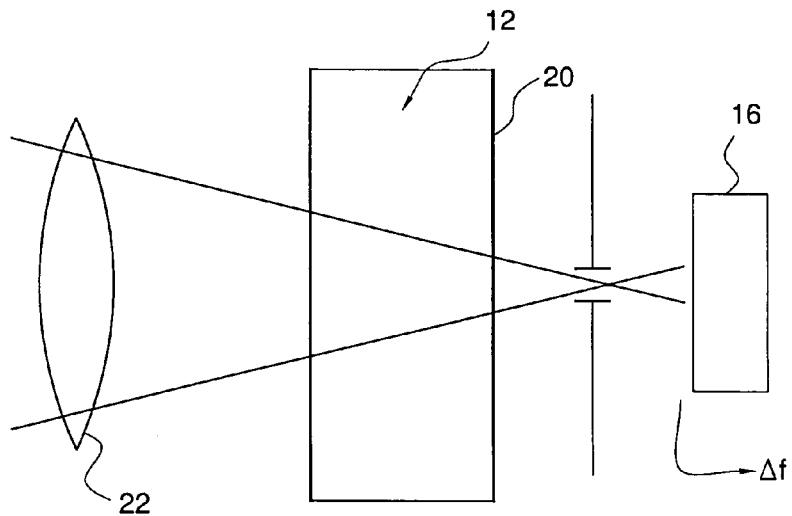
Figure 3C:
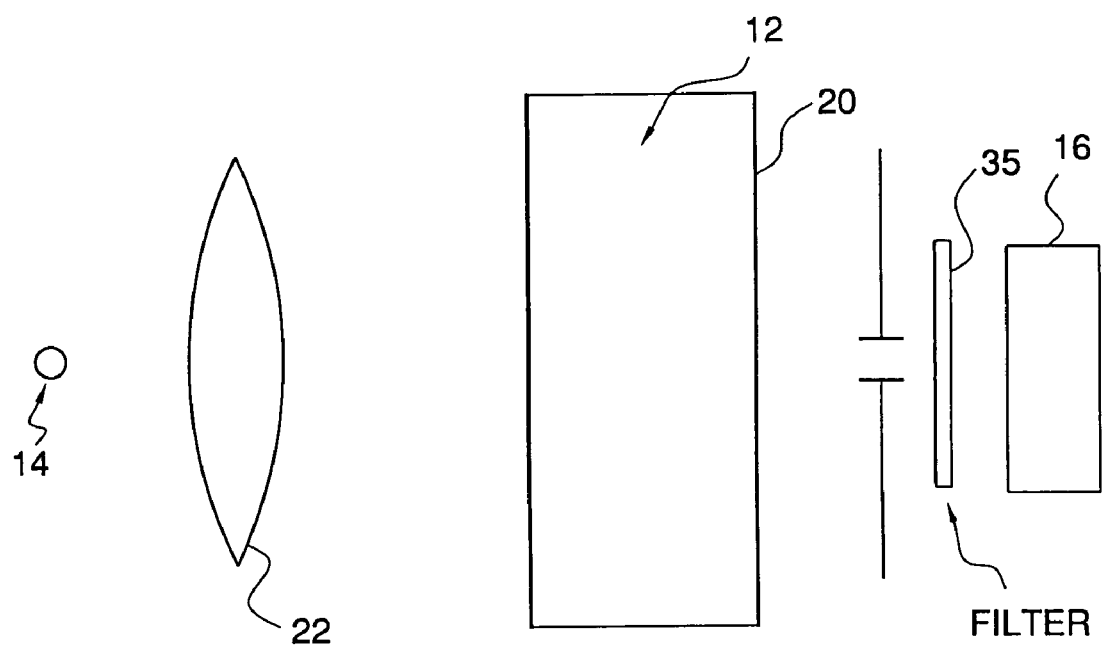

FIG. 3a; FIG. 3b, and FIG. 3c, show alternate arrangements of a light source 14 and the detector 16 as well as one or more lenses that would work under certain circumstances. FIG. 3a has the first lens 22, the aperture 26, and the collimating lens 28. FIG. 3b does not have the collimating lens 28 and so the detector 16 must be able to handle light that has not been collimated. In this scenario, it may be more difficult to determine a unique solution due to the presence of higher order distortions. The same would be true if the collimating lens 28 was present but the aperture 26 was removed. The aperture 26 is not required in certain circumstances. FIG. 3c adds a filter 35 so that a white light source can be used without a filter at the source but with some sort of filter at the detector 16. The detector filter could even be an electronic device or involve an algorithm.

Figure 4:
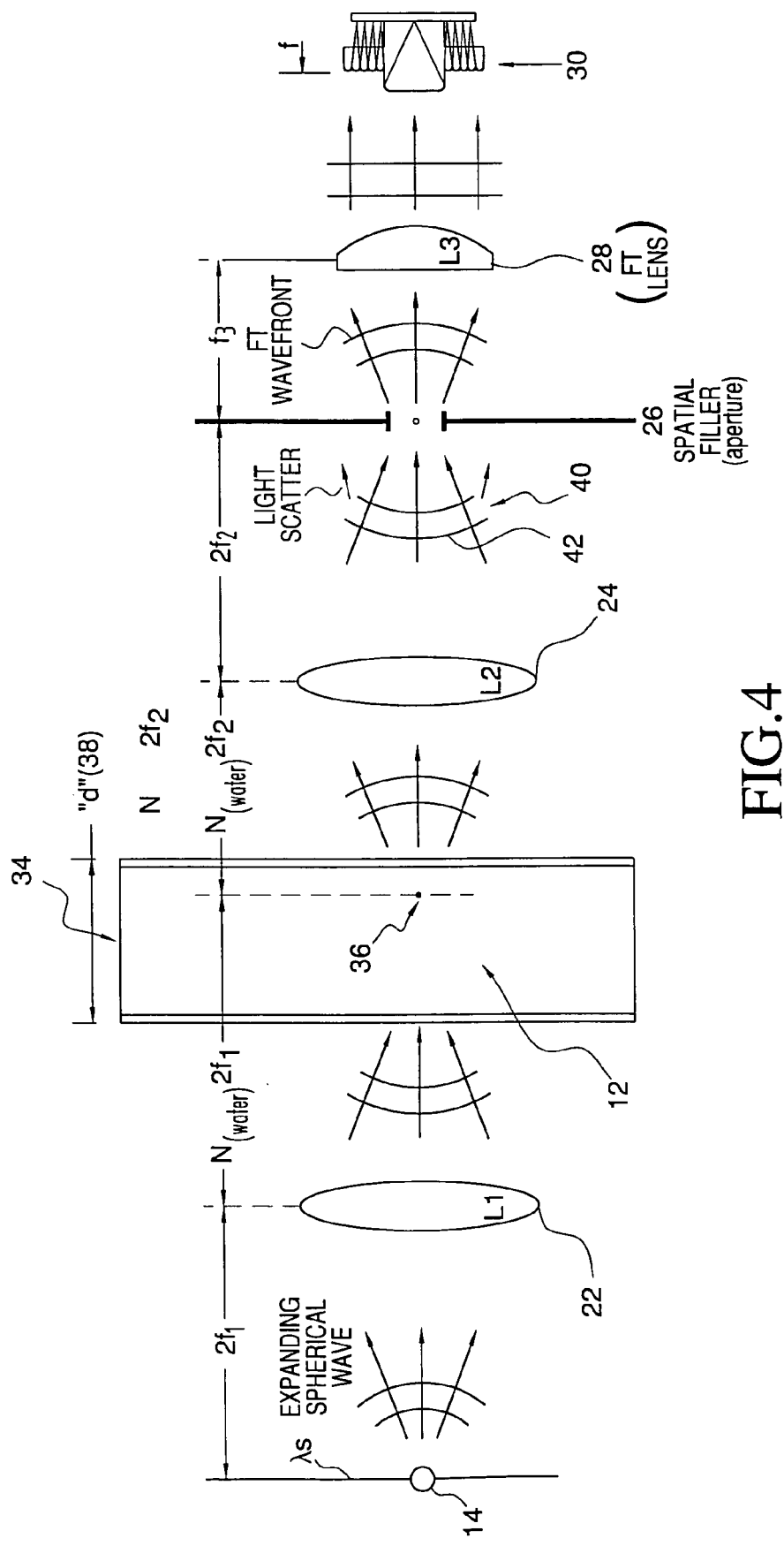
FIG. 4 is a schematic diagram of one embodiment of the biological imager with an area sensor and lens array.

FIG. 4 shows the light source 14 directed toward the first collimating lens ($L_1$) 22 which in this case is shown to be at a distance that is twice its focal length from the light source. The first lens could be any distance from the light source as would be known in the art as long as the expanding wave front is known as it enters the biological mixture 12. The wave front will be refracted by the first lens 22, refracted through the biological mixture 12, and in this embodiment, if refracted through pure water, would focus at a point 36 between the first lens 22 and the second lens 24. The focus point 36, if it was pure water, would be $N_{water}$ (refractive index of water)·$2·f_1$ (focal length of the first lens 22) from the first lens 22, and a distance equal to $N_{water}$ (refractive index of water)·$2·f_2$ (focal length of the second lens 24) from the second lens 24. The lenses 22 and 24 are separated by a distance "d" shown by 38. The emerging light would be refracted by the second lens 24 and directed toward the spatial filter 26, which in this embodiment is a distance equal to $2·f_2$ from the second lens 24. After passing through the biological imager 10 the light wave front has been distorted by scattering in the fluid. The distorted wave front represented by 40 in the diagram would defocus by higher order terms incorporated in it, as shown in the diagram by the wavy line 42. After this distorted wave front 40 passes through the spatial filter or aperture 26, the wave front has some of the noise eliminated leaving biological fluid mixture dependent defocus. The choice of an aperture or spatial filter 26 is critical to the success of this apparatus because, like a confocal microscope, it eliminates noise (higher order distortions) without removing the focus information. If the aperture is too small, the information that includes the mixture dependent focus would be lost; but if the aperture is too large, unnecessary noise would detract from the efficiency of the apparatus. All of the distances must be measured precisely since the shift in the focal point will be the order of a wavelength.

The filter aperture requirements (size, geometry, etc.) are heavily dependent on the optical system layout and the defined measurement tolerances. Given that defocus shifts are the primary wavefront aberration to be measured, all other contributions to the WFE (wavefront error) can be ignored. The filter aperture 26 can help reduce the other aberrations (typically, of a higher order than defocus), which are primarily due to scattering generated by the material being measured. A basic review of how to deal with such things can be found in Goodman's book "Introduction to Fourier Optics", in chapter and section: "Frequency analysis of optical imaging systems, Aberrations and their effects on frequency response" (Chapter 6–4 in the $1^{st}$ edition). Here, the generalized exit pupil function is defined as:

$$P(x_p,y_p)=p(x_p,y_p)\exp(jkW(x_p,y_p)), \text{ where } p(x_p,y_p)$$

is the non-aberrated pupil function applied to the image at aperture 26. $W(x_p,y_p)$ encompasses the aberration phase terms of the exit pupil wavefront. Assuming defocus is the dominant term we have:

$$W(x_p, y_p) = \frac{\varepsilon(x_p^2 + y_p^2)}{2} + \text{Higher order terms},$$

where $\epsilon$ is the phase error term. The specified shifts in defocus are related to $\epsilon$ and an aperture 26 can be constructed such that the higher order contributions are minimized with respect to the desired measurable defocus range.

In this embodiment the third collimating lens 28 (also referred to as "a fourier transform lens" or "FT lens") is placed a distance equal to its focal length from the spatial filter 26. The third, collimating lens 28 essentially turns the wave front "inside out" and the focus information is the largest component of the light wavefront leaving the collimating lens 28. The light is focused on the lens array 30 of this embodiment which could take many different formats (such as Shack-Hartmann, Interferometry phase diversity, various algorithms, electric circuits, etc.). A Shack-Hartmann area sensor 32 can perform inverse fourier transform resulting in spot shifts when a refractive index of the biological mixture 12 changes. If the parameters are carefully chosen and tuned so that there is no shift when the medium is water, and there is a positive shift when there is the presence of certain components and there is a negative shift when there is the presence of other components allowing a simple deflection measurement to determine the fraction of certain components in a sample. The area sensor 32 could take another format such as interferometer, which would require the transmission of an undistorted wavefront from the light source 14 to the detector 16 to the area sensor 32 in order to get the interference necessary for the interferometer to work. In which case, there would be no need for the collimating lens 28.

Figure 5A:
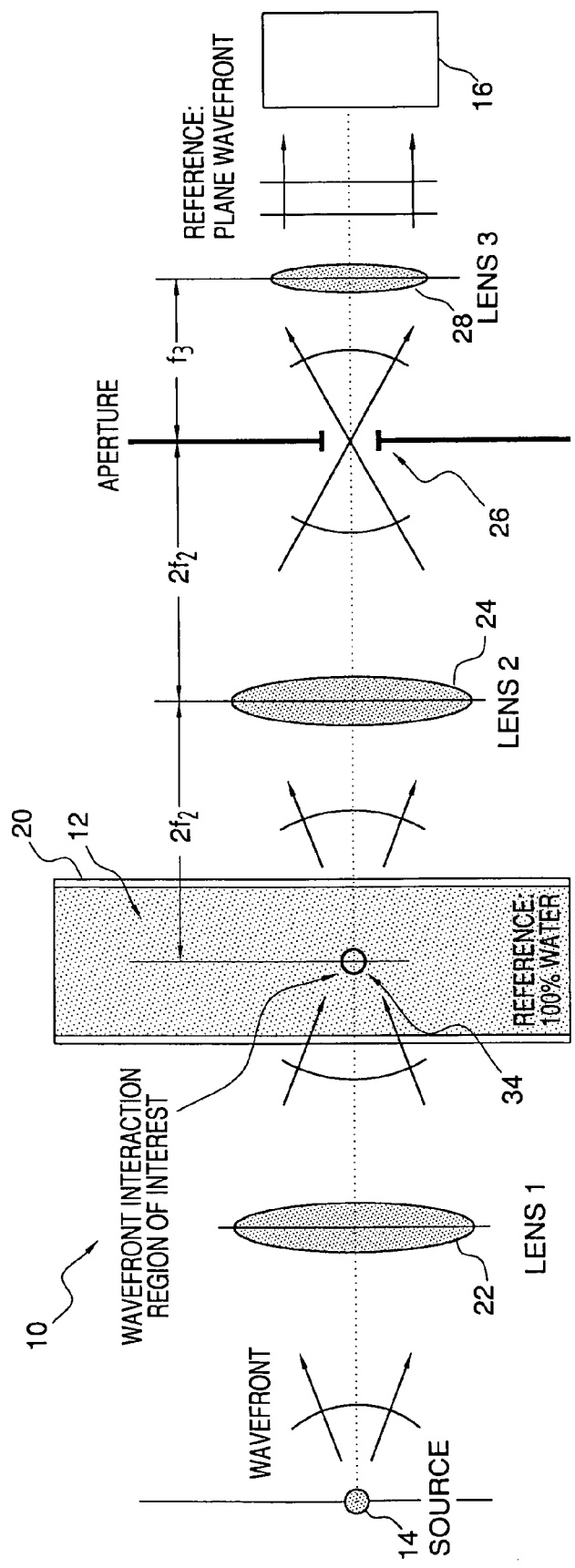
FIG. 5a is a schematic of the biological imager with a reference fluid.

FIG. 5a is a schematic diagram of the biological imager 10 and a reference fluid with a known refractive index such as water, calibrated so that the focus of the light passed through at the detector 16.

Figure 5B:
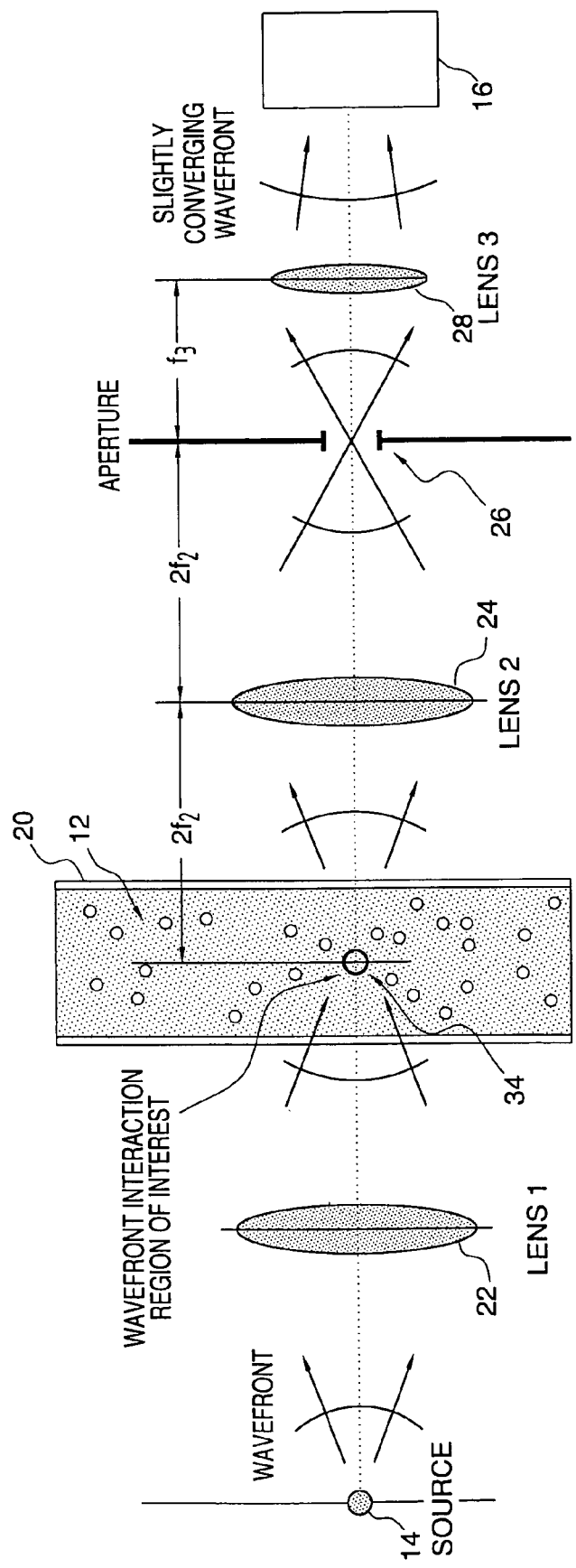
FIG. 5b is a schematic of the biological imager with the reference material and another lighter fluid.

FIG. 5b is a schematic drawing of the biological imager 10 and both the reference fluid and another lighter fluid such that the focal point changes in relation to the change in refractive index due to the amount of biological components in the mixture.

Figure 5C:
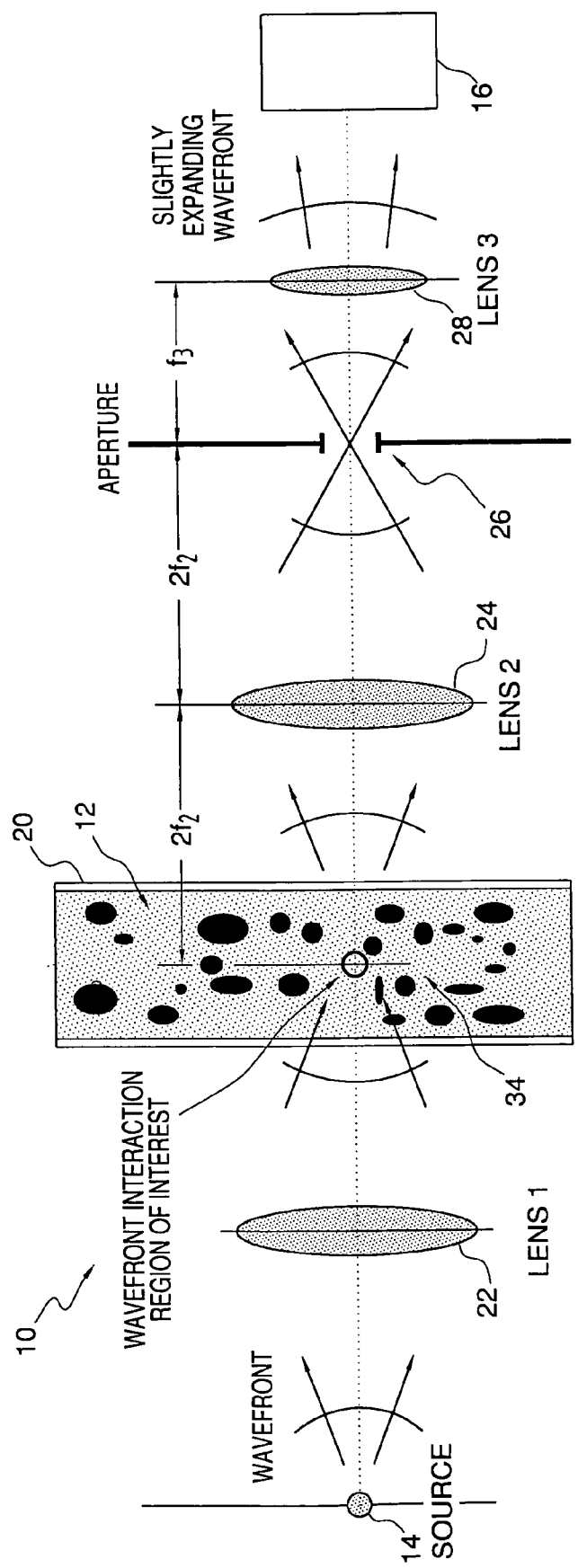
FIG. 5c is a schematic drawing of the biological imager with the reference material and another heavier fluid.

FIG. 5c is a schematic drawing of the biological imager 10 and both the reference fluid and another heavier fluid such that the focal point changes in relation to the change in refraction index due to the heavier fluid. Note that the focal point will shift in a direction opposite of that in FIG. 4b in this example. The introduction of the lighter gas causes less refraction because the light is traveling through a fluid with a lower refractive index.

Figure 5D:
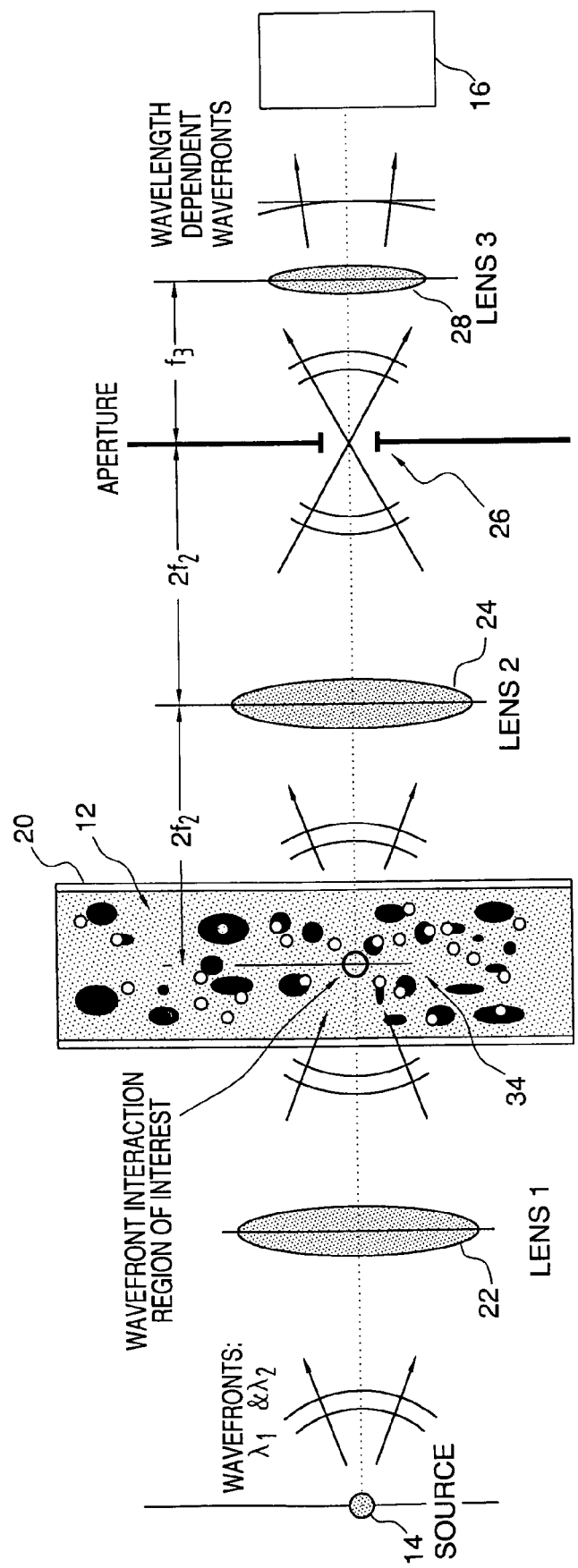
FIG. 5d is a schematic of the biological imager with the reference material and with both a lighter and a heavier fluid.

FIG. 5d is a schematic drawing of the biological imager 10 and the reference fluid, as well as both a lighter and a heavier fluid so that there is the need to focus two different wavelengths of light to solve for the two unknown fractions of biological components present.

Figure 5E:
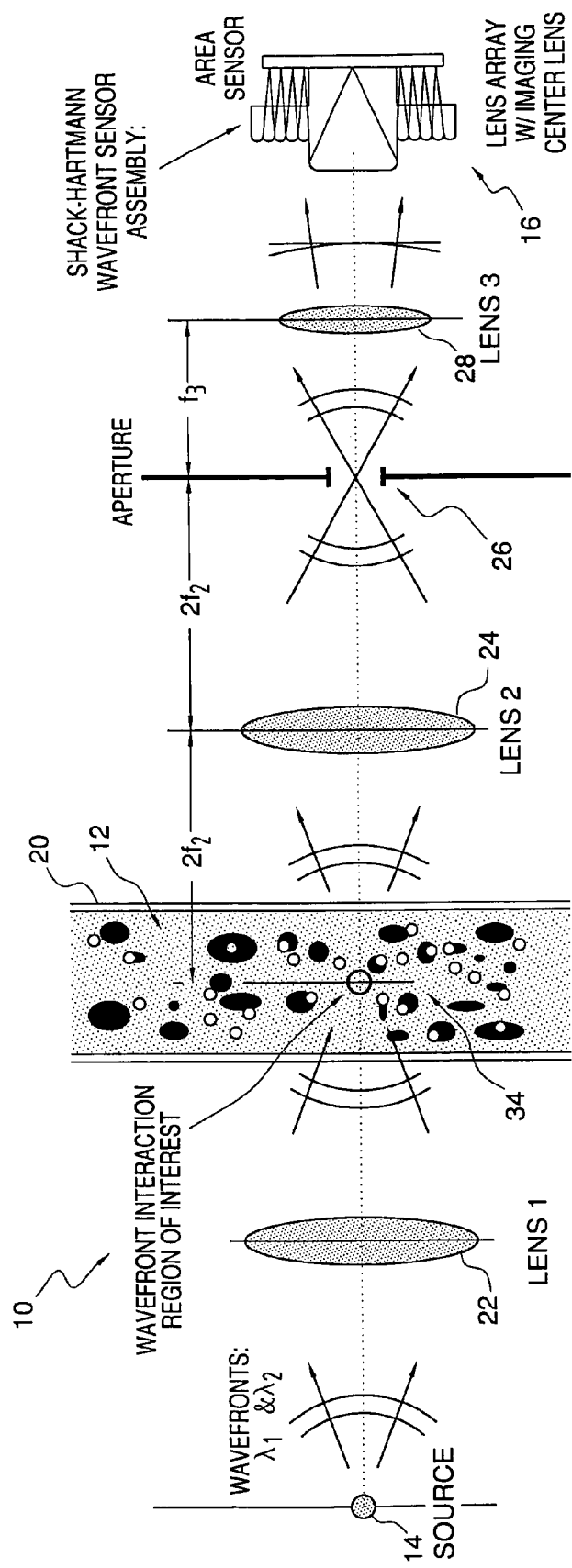
FIG. 5e is a schematic drawing of the biological imager and a Shack-Hartmann detector.

FIG. 5e is a schematic drawing of the biological imager 10 with all three phases of fluid and a Shack-Hartmann detector.

Figure 6:
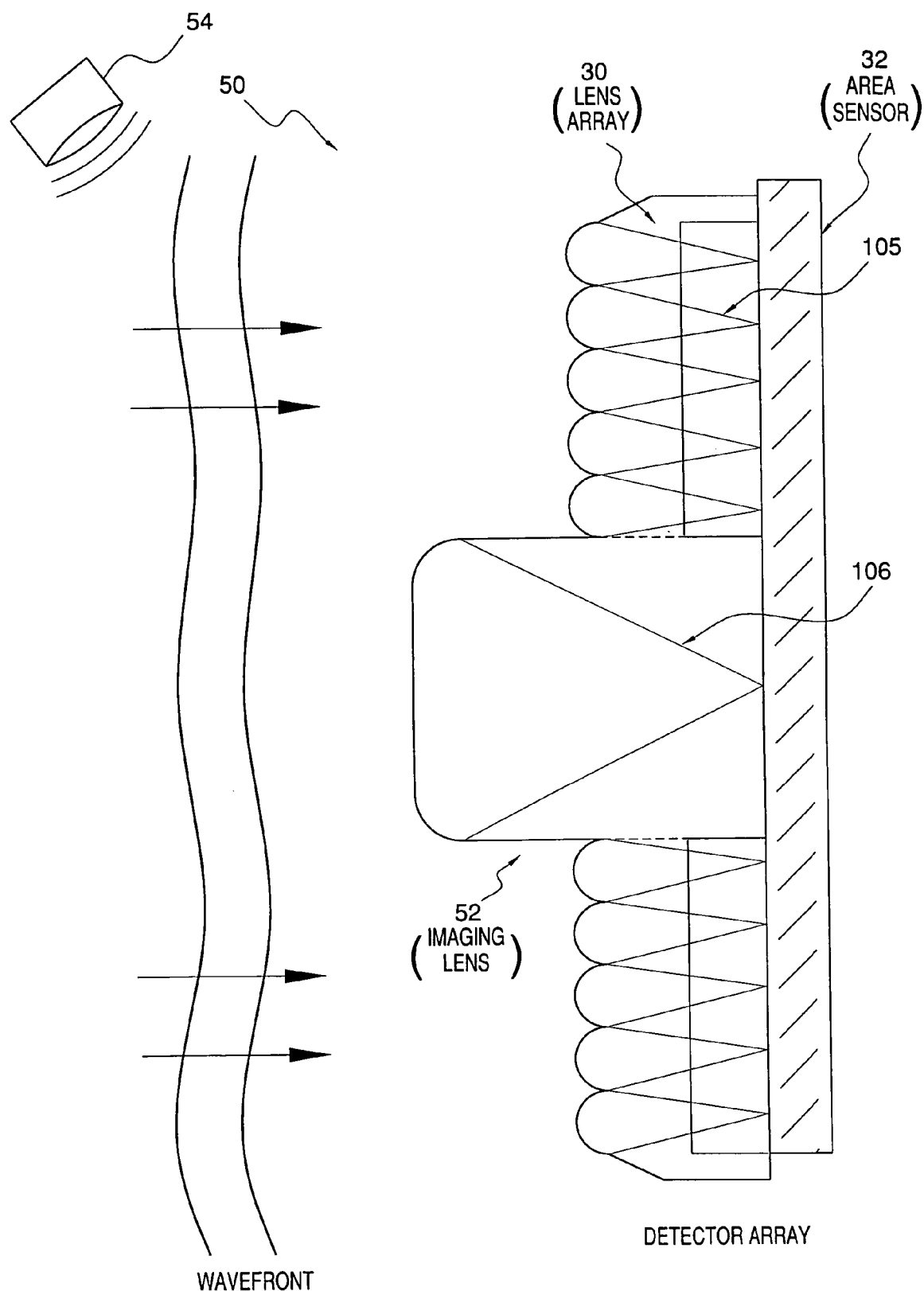
FIG. 6 is an embodiment with an imaging lens.

The biological imager 10 of FIG. 6 is set to analyze a fluid flow of a biological mixture. This biological system could be part of an organism. A sample from an organism, or it could be in a separate vessel or system in a laboratory. This is particularly effective in organisms because of the gel-like nature of living cytoplasm, the interior living cells. Many cellular functions can be attributed to and are accomplished by gel properties of sub-membrane cytoskeleton or actin, microtubules and other protein structures such as regulating ionic fluxes and concentrations. Cytoplasmic gels manifest collective phase transitions such as polymerization of actin proteins with accompanying ordering of cell water and exclusion of large cations. These collective phase transitions can explain not only ionic fluxes, but also voltage gradients, propagating action potentials, mitosis, muscle contraction and cell movement. The fact that cells include and are regulated by components such as the protein matrix-based gels make this invention particularly useful. Since the cytoplasm is intrinsically reactive and able to maintain cell homeostasis and functions, the cytoplasm gel best captures the essence of the living state and can be measured in response to the refractive index of light in accordance with this invention.

FIG. 7 shows a fluid stream that can be analyzed using this invention to determine the rate of flow.

Any properties that can be derived from the different refractive indices of the cellular components, particularly protein matrix-based gels. Properties such as the geometry of the structure in a bath of known refractive index using the refractive index of light is possible because the structure will refract light at the boundaries.

One embodiment of the method for measuring the biological fractions includes projecting two discrete wavelengths $\lambda_1$ and $\lambda_2$ through the biological components causing wavefront distortion allowing for the determination of two separate focal point displacements and the determination of two biological fractions in response to the measurements generated by $\lambda_1$ and $\lambda_2$. This method requires values of $\lambda_1$ and $\lambda_2$ such that:

(a) $\lambda_1$: chosen such that $N_{BC}(\lambda_1) \neq N_{water}(\lambda_1)$; $N_{BC}(\lambda_1) \neq N_{air}(\lambda_1)$; and (b) $\lambda_2$: chosen such that $N_{BC}(\lambda_2) \neq N_{water}(\lambda_2)$; $N_{BC}(\lambda_2) \neq N_{air}(\lambda_2)$.

In order to solve for one unknown, for example the fraction of DNA, the following equation is solved where:

(a) OPL=Optical Path Length (measured by the refractometer)

(b) OPL[measured]=$N_{avg}(\lambda)$;

(c) $AN_{BC1}(\lambda_1)+BN_{BC2}(\lambda_1)+CN_{BC3}(\lambda_1)=N_{avg}(\lambda_1)$;

(d) $AN_{BC1}(\lambda_2)+BN_{BC2}(\lambda_2)+CN_{BC3}(\lambda_2)=N_{avg}(\lambda_2)$;

(e) A+B+C=1

(f) $N(\lambda)$=refractive index.

In order for these equations to be solved, it is necessary that the fluid components do not chemically interact. This is characterized by being able to be separated with the component ratios preserved. In one example, when pure water is a reference point, the focal point changes as a function of the material in the flow stream. The light beam will curve (spread) when compared to the reference. This curvature can be measured. There are a number of combinations that can be solved for including a component refractive index or the ratio of components. If there are two or more unknowns then additional wavelengths like $\lambda_1$ and $\lambda_2$ will be required to solve for these additional unknowns.

First the first $\lambda_1$ is focused and the distance from the known focus in water measured so that $N_{avg}(\lambda_1)$ can be calculated. Subsequently, the second $\lambda_2$ is focused, the distance from the known focus measured, and $N_{avg}(\lambda_2)$ calculated. With all but A, B, and C known the coefficients A, B, and C can be calculated from the three equations.

If the refractive index of one biological component ($N_{BC2}$) is also unknown but the refractive indices of two other biological components ($N_{BC1}$ and $N_{BC3}$), are known, then there are four unknowns (A, B, C and $N_{BC2}$) since only $N_{BC1}$ and $N_{BC3}$ are known. To solve these equations, four wavelengths ($\lambda_1$, $\lambda_2$; $\lambda_3$, $\lambda_4$) must be focused and the distance from a known focal point measured for each [$N_{avg}(\lambda_1)$; $N_{avg}(\lambda_2)$, $N_{avg}(\lambda_3)$, $N_{avg}(\lambda_4)$]. The $N_{BC2}$ varies in a known way according to the Cauchy relationship such that:

$N(\lambda_1) \propto K_1 + K_2 N(\lambda_1^2)$, where the higher order terms are ignored, and then $N_{oil}$, A, B, and C can be solved for simultaneously. Including additional terms in the Cauchy expansion will require additional wavelengths in order to find a solution.

A detailed analysis using the physical arrangement shown in FIG. 2 follows:

a) Dimension Items (i) $s_{o1}$—Distance of light source (14) to the $1^{st}$ principle plane of Lens 1 (22)

(ii) $s_{i1}(N_{ave}(\lambda))$—Distance of imaged light source ($I_1$) to the $2^{nd}$ principle plane of Lens 1 (22) for $N_{ave}(\lambda)$ (iii) $s_{o2}(N_{ave}(\lambda))$—Distance of imaged light source ($I_1$) to $1^{st}$ principle plane of Lens 2 (24) for $N_{ave}(\lambda)$ (iv) $s_{i1ref}(N_{ref}(\lambda_{ref}))$—Reference distance of imaged light source ($I_1$) to $2^{nd}$ principle plane of Lens 1 (22) for $N_{ref}(\lambda_{ref})$ (v) $s_{o2ref}(N_{ref}(\lambda_{ref}))$—Reference distance of imaged light source ($I_1$) to $1^{st}$ principle plane of Lens 2 (24) for $N_{ref}(\lambda_{ref})$ (vi) $\Delta s_{i1}(\lambda)$—Change in $s_{i1}$ relative to reference at $s_{i2ref}$ due to wavelength and material changes between Lens 1 (22) and Lens 2 (24)

(vii) d—Thickness of the material to be analyzed (viii) $s_{i2}(N_{ave}(\lambda))$—Distance of imaged light source (12) to the $2^{nd}$ principle plane of Lens 2 (24) for $N_{ave}(\lambda)$ (ix) $s_{i2ref}(N_{ref}(\lambda_{ref}))$—Reference distance of imaged light source ($I_2$) to $2^{nd}$ principle plane of Lens 2 (24) for $N_{ref}(\lambda_{ref})$ (x) $\Delta s_{i2}(N_{ave}(\lambda))$—Change in $s_{i2}$ relative to reference at $s_{i2ref}$ due to wavelength and material changes between Lens 1 (22) and Lens 2 (24)

(xi) $f_3$—Effective focal length of Lens 3 (28)

(xii) α—Aperture size (xiii) $s_{o3}(N_{ave}(\lambda))$13 Distance of imaged light source (12) to $1^{st}$ principle plane of Lens 3 (28) for $N_{ave}(\lambda)$ (xiv) z—Distance from aperture 26 to where the WFE (wavefront error) is measured (xv) y—Distance perpendicular from optical center line to where the WFE is measured (xvi) WFE(λ)—Paraxial Wavefront Error (measured in waves of $\lambda_{ref}$) relative to reference due to wavelength and material changes between Lens 1 (22) and Lens 2 (24)

b) Glossary:

(i) λ≡Wavelength (ii) $\lambda_{ref}$≡Reference wavelength (iii) N≡Refractive index (iV) f≡Effective focal length for all λ to be used in device, where f>0 for all lenses (v) $N_{ref}(\lambda_{ref})$≡Index of a reference component (m=0) at a reference wavelength ($\lambda_{ref}$)

(vi) $A_m$≡Solution component volume percentage (vii) n≡Number of solution components c) Known Terms:

(i) $\lambda_{ref}$, $N_{ref}(\lambda_{ref})$, $f_1$, $f_2$, $f_3$, $s_{o1}$, and d d) Equations:

$$\text{(i)}\quad N_{ave}(\lambda) = N_{ref}(\lambda_{ref}) + \Delta N_{ave}(\lambda) = \sum_{0}^{n-1} A_m N_m(\lambda)$$

$$\text{(ii)}\quad s_{refi2}(\lambda) = \frac{df_2 - N_{ref}(\lambda_{ref}) f_1 f_2 s_{o1} / (s_{o1} - f_1)}{d - N_{ref}(\lambda_{ref})[f_2 - f_1 s_{o1} / (s_{o1} - f_1)]}$$

$$\text{(iii)}\quad s_{i2}(\lambda) = \frac{df_2 - N_{ave}(\lambda) f_1 f_2 s_{o1} / (s_{o1} - f_1)}{d - N_{ave}(\lambda)[f_2 - f_1 s_{o1} / (s_{o1} - f_1)]}$$

$$\text{(iv)}\quad \Delta s_{i2}(\lambda) = s_{refi2}(\lambda) - s_{i2}(\lambda) = \frac{df_2 - N_{ref}(\lambda_{ref}) f_1 f_2 s_{o1} / (s_{o1} - f_1)}{d - N_{ref}(\lambda_{ref})[f_2 - f_1 s_{o1} / (s_{o1} - f_1)]} - \frac{df_2 - N_{ave}(\lambda) f_1 f_2 s_{o1} / (s_{o1} - f_1)}{d - N_{ave}(\lambda)[f_2 - f_1 s_{o1} / (s_{o1} - f_1)]}$$

(v) $s_{o3}(\lambda)=f_3-\Delta s_{i2}(\lambda)$ $$\text{(vi)}\quad s_{i3}(\lambda) = \frac{s_{o3} f_3}{s_{o3} - f_3} = f_3 - \frac{f_3^2}{\Delta s_{i2}(\lambda)}$$

$$\text{(vii)}\quad WFE(\lambda) = \frac{|s_{i3}(\lambda) - z| - \sqrt{(s_{i3}(\lambda) - z)^2 - y^2}}{\lambda_{ref}} = \frac{1}{\lambda_{ref}}\left[\left|f_3 - \frac{f_3^2}{\Delta s_{i2}(\lambda)} - z\right| - \sqrt{\left(f_3 - \frac{f_3^2}{\Delta s_{i2}(\lambda)} - z\right)^2 - y^2}\right]$$

e) Number Run:

(i) $s_{o1}$=100 mm (ii) $\lambda_{ref}$=1.4 μm (iii) d=260 mm (iv) y=10 mm (v) z=50 mm (vi) $f_1=f_2=f_3$=50 mm (vii) $N_0(\lambda_{ref})$=1.3

(viii) $N_{ave}(\lambda)$=1.302

(ix) $\Delta s_{i2}(N_{ave}(\lambda))$=0.03691172 mm; ∴ WFE(λ)≈0.53 Waves@ $\lambda_{ref}$ Most wavefront sensors can easily measure errors to less than 1 wave, and given a small change of index, there is typically a significant change in the wavefront error produced. For the above case, where there is a 0.002 index change, the WFE is easily measurable.

Other properties that can be calculated include any physical property that has a relationship that changes with the refractive index. The refractive index relates to the interaction of light with the electrons in a substance, the more electrons, and the more polarizable the electrons, the higher the refractive index. Although viscosity is resistant to the shearing force, it is related to the interactions between molecules as they move past one another. It is possible to relate viscosity and other properties to the refractive index of light within a specific class of components, specifically proteins for example, by correlating the two properties and using the relationship. For example, for proteins, the viscosity increases because there is more opportunity for them to interact as they are moving past each other, and the refractive index also increases slightly because the density of electrons is a little higher. For this very restricted class, a correlation can be made that is valid for that class of proteins. Similar correlations could be made for other non-immiscible components.

In order for these equations to be solved, it is necessary that the fluid components do not chemically interact, such that the biological component may be separated with the component ratios preserved. For example, when pure water is a reference fluid, the focal point changes as a function of the material in the flow stream. The light beam will curve (spread) when compared to the reference fluid. This curvature can be measured. There are a number of combinations that can be solved including a refractive index or a ratio of non-immiscible biological component fractions. If there are two or more unknowns then additional wavelengths will be required to solve for the unknown.

The Shack-Hartmann Wavefront Analyzer is constructed by placing an array of apertures in front of a charge-coupled device or CCD camera. These apertures allow light be diffracted by the plate onto the CCD. The segments of the beam that pass through the apertures will be spatially displaced from the center position, based on the direction of travel, or the phase of that part of the beam. The CCD camera measures the phase of each spot by measuring this displacement. Software algorithms then reconstruct a wavefront for the entire beam. The spacing of the apertures defines the resolution of the system, and the size of each aperture is calculated to optimize sensitivity to phase changes. In contrast, a Shack-Hartmann Wavefront Analyzer uses an array of small lenslets to collect all of the beam in each aperture position, and project all of it onto a detector.

Essentially, a spherical wavefront is refracted through the biological mixture 12, which will eventually be focused. It is preferred that the focus be located within the biological mixture 12. A key component is the aperture or spatial fluid 26 which eliminates the majority of the (waste) scattered light outside of the focus region. The aperture or spatial filter 26 functions as a noise filter. This is how confocal microscopy works. Additionally, the aperture size is optimized to account for focus shifts (+ or −) due to average volume index changes. Any wavefront can be propagated through the test region, if the wavefront is pre-determined before being transmitted through the distortion zone (e.g., a component-water mix), and if there is a reference volume of material (e.g., water) to make a comparison with. A distortion dependent shift in focus (defocus) is going to be the largest distortion component, hence, the easiest to detect and measure (even in a noisy environment).

Not only can the refractive index or relative fractions of components be calculated but other relative functions like thickness, size, geometry, and viscosity of the cellular components such as different fluids or gels such as the protein matrix-based gels.

Concerning a flow rate measurement method, a strobe will be used as shown in FIG. 7 and accommodations made for the boundary effects in the container or flow tube. The flow profile can be compensated by taking the flow rate at the center of the container or flow tube and at the edges and averaging, or testing at the center. LED's are strobed at different duty cycles until particles appear stationary (within a certain tolerance). Hence, the velocity of the fluid can be determined. The sensing array can have a central imaging lens to detect the flow rate and wavefront sensor lenslets to detect the wave front information and distortions. With a fixed imaging optic, the device measures the velocity of particulate matter in the focus region in the fluid using a strobe. If the fluid ratios and component values are known, the volume fluid flow rate can be calculated if the center flow rate has been determined. By varying the gate time of the strobe, imaged particles may appear stationary once the gate time is correct.

With a fixed imaging optic, the device measures velocity of particulate matter in the focus region in the fluid using a strobe. With knowledge of the fluid ratios, and density values, the fluid volume flow can be determined. It is also possible to scan the imaging optic (using a speaker coil mounted optic as used in CD players) and collect a range of flow data.

A number of basic improvements result, which include:
a) reduction of errors due to optical scattering losses;
b) simplification of instrument calibration;
c) improved accuracy for low-water-cut (higher ratio of biological component to water).
d) elimination of calibration step;
e) accurate multi-component detection system over all ratios; and
f) flow measurements (if required).

While the invention has been described in connection with a presently preferred embodiment thereof, those skilled in the art will recognize that many modifications and changes can be made therein without departing from the true spirit and scope of the invention, which accordingly is intended to be defined solely by the appended claims.

The invention claimed is:

1. A method of determining the amounts of first and second non-immiscible components in a mixture having known, different indices of refraction in the mixture comprising:
a) passing a focused light beam through the mixture;
b) measuring the displacement of the actual point of focus from a known focal point through a material with a known index of refraction; and
c) calculating the amounts of the first and second components present from the displacement.

2. The method of determining the amounts of the non-immiscible components present in a mixture as set forth in claim 1, comprising:
a) passing a focused light beam having at least two discrete wavelengths through the mixture; and
b) separately measuring the displacement of the actual point of focus from a reference focal point for each of said at least two discrete wavelengths.

3. The method of determining the amounts of biological components present as set forth in claim 1, comprising:
filtering the emergent light beam to remove higher order distortions.

4. The method of determining the amounts of biological components present as set forth in claim 1, comprising:
collimating the beam after it passes through the biological components and before measuring the displacement of the focal point.

5. The method of determining the amounts of biological components as set forth in claim 4, in which measuring the displacement comprises measuring the shape of a collimated wavefront beyond the point of focus.

6. A method for measuring characteristics of a biological system having at least two contrasting density components comprising:
(a) projecting light of wavelength $\lambda_1$ through a multi-density system to distort wavefront of wavelength $\lambda_1$;
(b) projecting light of wavelength $\lambda_2$ through a multi-density;
(c) system to distort a wavefront of wavelength $\lambda_2$; and
(d) determining biological components information in response to the distortion of the light of wavelengths $\lambda_1$ and $\lambda_2$,
wherein the biological information determines the refractive index of a biological component.

7. A method for measuring characteristics of a biological system having at least two contrasting density components comprising:
(a) projecting light of wavelength $\lambda_1$ through a multi-density system to distort wavefront of wavelength $\lambda_1$;
(b) projecting light of wavelength $\lambda_2$ through a multi-density;
(c) system to distort a wavefront of wavelength $\lambda_2$; and
(d) determining biological components information in response to the distortion of the light of wavelengths $\lambda_1$ and $\lambda_2$,
wherein the biological information determines the ratio of biological components.

8. A method for measuring characteristics of a biological system having at least two contrasting density components comprising:
(a) projecting light of wavelength $\lambda_1$ through a multi-density system to distort wavefront of wavelength $\lambda_1$;
(b) projecting light of wavelength $\lambda_2$ through a multi-density;
(c) system to distort a wavefront of wavelength $\lambda_2$; and
(d) determining biological components information in response to the distortion of the light of wavelengths $\lambda_1$ and $\lambda_2$,
wherein the biological information determines both the refractive index and the ratio of biological components.

9. A method of analyzing biological components in a system, having a plurality of contrasting density components comprising:
a) a projecting light comprising $\lambda_1$ and $\lambda_2$ through the fluid stream such that (i) $\lambda_1$: chosen such that $N_{BC}(\lambda_1) \neq N_{water}(\lambda_1)$ and $N_{BC}(\lambda_1) \neq N_{air}(\lambda_1)$;

(ii) $\lambda_2$: chosen such that $N_{water}(\lambda_2) \neq N_{water}(\lambda_2)$ and $N_{BC}(\lambda_2) \neq N_{air}(\lambda_2)$;

b) projecting light through the system such that displacement of the focus from a known position indicates a specific biological component;

c) further projecting light through an aperture and collimating lens array to an area sensor; and d) detecting the wavefront shape distortions to determine the specific biological components.

10. The claim of claim 9, further comprising using a strobe to determine movement of the components.

11. A method of analyzing biological components in a system, having a plurality of contrasting density components comprising:

a) a projecting light comprising $\lambda_1$ and $\lambda_2$ through the fluid stream such that (i) $\lambda_1$: chosen such that $N_{BC}(\lambda_1) \neq N_{water}(\lambda_1)$ and $N_{BC}(\lambda_1) \neq N_{air}(\lambda_1)$;

(ii) $\lambda_2$: chosen such that $N_{water}(\lambda_2) \neq N_{water}(\lambda_2)$ and $N_{BC}(\lambda_2) \neq N_{air}(\lambda_2)$;

b) projecting light through the system such that the focus indicates a specific biological component;

c) further projecting light through an aperture and collimating lens array to an area sensor; and d) detecting the wavefront distortions to determine the specific biological components, further comprising tuning the detector to detect a plane wave when projected through water.

12. A biological imager for measuring the biological components in a system comprising:

a) a light source comprising wavelengths $\lambda_1$ and $\lambda_2$ such that when projected through the biological sample, produces a distinct signature due to the distortion of the wavefront; and b) detection to sense the signature, wherein a focus moves left or right to indicate more or less of a component.

13. The claim of claim 12, further comprising using a Shack-Hartmann Wavefront Analyzer.

14. The claim of claim 12, further comprising solving the first order differential equations.

* * * * *